(12) United States Patent
Hazelwood et al.

(10) Patent No.: US 11,612,351 B2
(45) Date of Patent: Mar. 28, 2023

(54) ELECTROTHERAPEUTIC TREATMENT

(71) Applicant: NEUX TECHNOLOGIES, INC.

(72) Inventors: Vikki Hazelwood, West Palm Beach, FL (US); John Kubel, West Palm Beach, FL (US); Angela Gagliardi, West Palm Beach, FL (US); Scott Minnear, West Palm Beach, FL (US)

(73) Assignee: NEUX TECHNOLOGIES, INC., West Palm Beach, FL (US)

( * ) Notice: Subject to any disclaimer, the term of this patent is extended or adjusted under 35 U.S.C. 154(b) by 387 days.

(21) Appl. No.: 16/097,380

(22) PCT Filed: Apr. 27, 2017

(86) PCT No.: PCT/US2017/029917
§ 371 (c)(1),
(2) Date: Oct. 29, 2018

(87) PCT Pub. No.: WO2017/189890
PCT Pub. Date: Nov. 2, 2017

(65) Prior Publication Data
US 2019/0142337 A1  May 16, 2019

Related U.S. Application Data

(60) Provisional application No. 62/328,204, filed on Apr. 27, 2016, provisional application No. 62/328,201, filed on Apr. 27, 2016.

(51) Int. Cl.
*A61N 1/36* (2006.01)
*A61B 5/00* (2006.01)
(Continued)

(52) U.S. Cl.
CPC .............. *A61B 5/4833* (2013.01); *A61B 8/06* (2013.01); *A61B 8/4444* (2013.01); *A61B 8/461* (2013.01);
(Continued)

(58) Field of Classification Search
CPC ......... A61B 5/4833; A61B 8/06; A61B 8/461; A61B 8/4444; A61B 8/485; A61B 8/488;
(Continued)

(56) References Cited

U.S. PATENT DOCUMENTS 5,107,835 A  4/1992  Thomas
5,109,848 A  5/1992  Thomas et al.
(Continued)

FOREIGN PATENT DOCUMENTS

WO  2011077466 A1  6/2011

OTHER PUBLICATIONS

International Search Report for International Application No. PCT/US2017/029917, 4 pages, dated Sep. 28, 2017.
(Continued)

*Primary Examiner* — Patricia J Park
*Assistant Examiner* — Adil Partap S Virk
(74) *Attorney, Agent, or Firm* — Nixon Peabody LLP

(57) ABSTRACT

Systems and methods for locating, assessing, diagnosing, treating and monitoring of musculoskeletal disorders, soft tissue injuries, pain and other areas of dysfunctional tissue in patients, are provided. In the systems and methods, such assessments and treatments are performed using a combination of electrical stimulation and imaging tools.

10 Claims, 16 Drawing Sheets

(51) Int. Cl.
*A61N 1/04* (2006.01)
*A61B 8/00* (2006.01)
*A61B 8/08* (2006.01)
*B06B 1/06* (2006.01)
*A61B 8/06* (2006.01)

(52) U.S. Cl.
CPC .............. *A61B 8/485* (2013.01); *A61B 8/488* (2013.01); *A61N 1/0452* (2013.01); *A61N 1/36* (2013.01); *A61N 1/36003* (2013.01); *A61N 1/36014* (2013.01); *B06B 1/06* (2013.01); *B06B 2201/76* (2013.01)

(58) Field of Classification Search
CPC ... A61B 5/395; A61B 8/5246; A61B 5/02007; A61B 5/442; A61N 1/3603; A61N 1/36; A61N 1/36014; A61N 1/36003; A61N 1/0452; A61N 2007/0026; B06B 1/06; B06B 2201/76
See application file for complete search history.

(56) References Cited

U.S. PATENT DOCUMENTS

| | | | |
|---|---|---|---|
| 6,450,959 | B1 | 9/2002 | Mo et al. |
| 6,511,427 | B1* | 1/2003 | Sliwa, Jr ............. A61B 5/4869 600/438 |
| 8,768,474 | B1 | 7/2014 | Thompson et al. |
| 11,033,218 | B2* | 6/2021 | Gharib ................ A61B 5/4041 |
| 2004/0024312 | A1 | 2/2004 | Zheng |
| 2004/0220645 | A1* | 11/2004 | Freed ................ A61N 1/36014 607/48 |
| 2006/0163680 | A1 | 7/2006 | Chen |
| 2007/0293918 | A1* | 12/2007 | Thompson ........... A61N 1/0476 607/72 |
| 2008/0119737 | A1* | 5/2008 | Urbano ................. G01S 7/003 600/459 |
| 2010/0004715 | A1* | 1/2010 | Fahey ................. A61H 39/002 607/152 |
| 2010/0280371 | A1* | 11/2010 | Lacoste ................ H02K 47/04 600/437 |
| 2011/0054562 | A1* | 3/2011 | Gliner ................. A61N 1/0551 607/45 |
| 2011/0082524 | A1 | 4/2011 | Thomas et al. |
| 2011/0137166 | A1 | 6/2011 | Klee et al. |
| 2013/0245486 | A1* | 9/2013 | Simon ................. A61B 5/4836 607/46 |
| 2013/0274832 | A1* | 10/2013 | Manion .................... A61B 8/12 607/72 |
| 2014/0058292 | A1* | 2/2014 | Alford ..................... A61N 7/00 601/2 |
| 2014/0336730 | A1* | 11/2014 | Simon ................. A61N 1/0472 607/72 |
| 2015/0126865 | A1* | 5/2015 | Murai ................. A61B 8/0891 600/437 |
| 2015/0238165 | A1* | 8/2015 | Hyuga ................ A61B 8/4245 600/449 |
| 2015/0360039 | A1* | 12/2015 | Lempka ............. A61N 1/37264 607/59 |
| 2018/0296185 | A1* | 10/2018 | Cox ...................... A61B 8/5246 |

OTHER PUBLICATIONS

Supplementary European Search Report for European Application 17790457.0, dated Nov. 28, 2019.

Asil et al., "Changing cerebral blood flow velocity by transcranial Doppler during head up tilt in patients with diabetes mellitus," Clinical Neurology and Neurosurgery, Elsevier, 2007, vol. 109, pp. 1-6.

CN Office Action for Application No. 201780033452.1, dated Jun. 17, 2021, w/second Office Action Summary.

Bharat et al., "Radiofrequency electrode vibration-induced shear wave imaging for tissue modulus estimation: A simulation study (L)"; journal of the Acoustical Society of America, 128 (4), Oct. 2010, pp. 1582-1585.

* cited by examiner

ELECTROTHERAPEUTIC TREATMENT

CROSS-REFERENCE TO RELATED APPLICATIONS

This application is a 371 National Stage Application of International Application No. PCT/US17/029917, filed Apr. 27, 2017, which claims priority to and the benefit of U.S. Provisional Patent Application Nos. 62/328,204 and 62/328,201, both filed Apr. 27, 2016 The contents of all of the above-identified applications are hereby incorporated by reference in their entireties as if fully set forth herein.

FIELD OF THE INVENTION

The present invention relates to systems and methods for locating, assessing, diagnosing, treating and monitoring of musculoskeletal disorders, soft tissue injuries, pain and other areas of dysfunctional tissue in patients, and more particularly systems for locating, assessing, diagnosing, treating and monitoring of musculoskeletal disorders, soft tissue injuries, pain and other areas of dysfunctional tissue in patients using a combination of electrical stimulation and imaging tools.

BACKGROUND

When a muscle (or other soft tissue) is injured or exists in a setting of inflammation for any reason, that tissue becomes dysfunctional. This dysfunctional tissue is fixed in spasm, meaning the muscle fibers are shortened and locked (unable to relax). These fibers become inhibited and unresponsive to the central nervous system's attempt to stimulate them to relax because the signals generated from the nerves are not strong enough. This dysfunctional area of the muscle eventually stops contracting and can no longer perform properly during any movement pattern. As a result, other areas of the muscle or an alternate muscle(s) must make up for this dysfunctional tissue. This usually leads to pain and injury in these and other areas as well. Moreover, abnormal motor patterns develop as these other muscles attempt to compensate for this dysfunction. Left untreated, these abnormal compensation patterns may become the default movement as time goes on.

It has long been known that the central nervous system operates significantly based on electrical impulses. The central nervous system works in two directions, both transmitting feeling sensation and pain to the brain, and in firing muscles responsive to impulses from the brain. It has also long been known that non-biological sources of electrical stimulation can be used to control certain muscles. For instance, the pacemaker works on this principle. Transcutaneous electrical stimulation has also been used in a variety of devices i.e. for increasing strength, density, size and endurance in muscles or the temporary relief of pain. In most applications, the placement of the electrodes and the electrical signal applied are pre-selected based upon a desired result or the site of where pain is felt.

Recently, there has been much interest in leveraging electrical stimulation to treat dysfunctional tissues and relieve pain and discomfort associated therewith, due to musculoskeletal disorders or soft tissue injuries. However, while providing electrical stimulation is relatively straightforward, diagnosing a dysfunctional tissue site requiring such electrical stimulation treatment and assessing the results of the electrical stimulation treatment can be relatively difficult.

DETAILED DESCRIPTION

Figure 1:
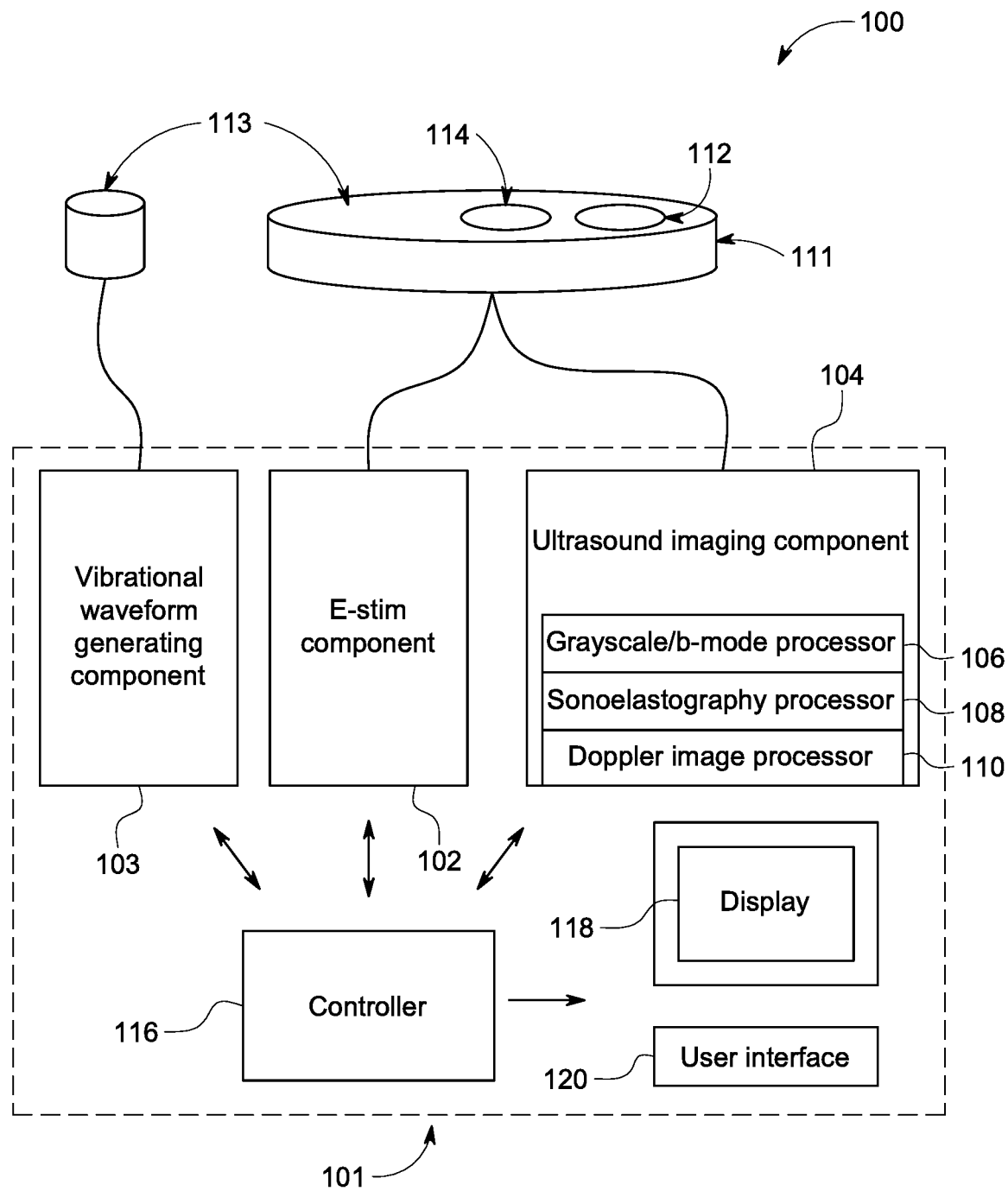
FIG. 1 is a block diagram of a system for implementing the various embodiments.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

In view of the foregoing, the present invention is directed to systems and methods for assessing or diagnosing, treating and monitoring musculoskeletal disorders, soft tissue injuries, pain and other areas of dysfunctional tissue in patients using electrical stimulation and/or ultrasound imaging, applying appropriate electrical stimulation based on such assessments and diagnoses, and evaluating the results of the electrical stimulation to determine whether additional stimulation is required.

In particular, the systems and methods described herein involve performing methodologies in real-time (or near-real time) that enable locating of site of an injury or other dysfunction requiring treatment and then measuring and assessing the results of the treatment. In some configurations, this can involve maintaining a precise location of the target site for treatment, i.e., the target site of injury or other dysfunction. It is this inability to perform such actions that are significant contributors to the difficulty experienced using existing processes.

To address the limitations and drawbacks of conventional mechanisms for locating, assessing, diagnosing, treating and monitoring musculoskeletal disorders, soft tissue injuries, pain and other areas of dysfunctional tissue, various embodiments are directed to systems and methods for performing a neuromuscular electrical stimulation in combination with an imaging modality, such as ultrasound imaging. The ultrasound imaging functions may be designed to image soft tissue structures such as muscles, blood vessels, nerves and the like in a manner that may be suitable for locating and/or treating dysfunctional tissue. For example, the ultrasound imaging capabilities of the system may provide such spatial and contrast resolution that is sufficient to distinguish nerves and blood vessels from surrounding tissue to a degree that is appropriate for the intended application. Additional features, such as the ability to produce an ultrasound image having color flow mode, may be provided. It should be noted that while the various embodiments will be primarily described with respect to ultrasound imaging, the various embodiments are not limited in this regard. Rather, the present disclosure contemplates that other types of existing and future imaging methodologies providing similar results may be used instead.

The techniques described herein for identifying treatment locations using electrical stimulus may be referred to as "neuromuscular interactive stimulation" or NIS. NIS involves a dynamic electrical stimulus with search capabilities that can locate dysfunctional tissue, which can be the source of pain and/or restricted range of motion. Once dysfunctional tissue is located, treatment involves placing electrodes at the dysfunctional tissue sites enabling the clinician to treat the source of pain and/or restricted range of motion versus where the pain is felt. Superimposing electrical stimulation onto voluntary muscle contractions—the patient performs the body motion that engages the muscles associated with where the dysfunctional tissue is found while the NIS stimulus is applied.

The systems and methods described herein are capable of performing electrical stimulation such as, for example, NIS as discussed above. It will be appreciated that NIS is discussed herein as one example of an electrical stimulation technique, and that an embodiment contemplates that the system may be used in connection with any type of electrical stimulation. The system may display information relating to the NIS features of the system on a display where ultrasound information and/or an ultrasound image may also be displayed. In addition, a probe of the system may include NIS controls, and/or the NIS electrodes themselves. The probe may be cordless or corded, depending on the application.

Turning first to FIG. 1 there is shown a block diagram of a system 100 for implementing a method in accordance with one aspect of the present invention. The system 100 includes a housing 101 for the various components of system 100. The housing 101 can be of any size, including hand held or portable sizes, and the components of system 100 can be sized accordingly. The various components can include an electrical stimulation (e-stim) component 102 to generate and provide the electrical stimulation for the patient. The e-stim component 102 can be configured in a variety of ways. Exemplary e-stim components and operation thereof are described in U.S. Pat. Nos. 5,107,835, 5,109,848, 8,768,474, and U.S. Patent Application Publication No. 2011/0082524, the contents of all of which are hereby incorporated by reference in their entirety.

The e-stim component 102 can be coupled to one or more electrodes 114 for providing the electrical stimulation treatment to the patient.

The components can further include an ultrasound (US) imaging component 104 for performing US scanning or sonography. The US imaging component 104 can be coupled to a transducer 112 for generating and receiving sound waves in a patient. Like a conventional US imaging component, the US imaging component 104 can be configured to include a grayscale or B-mode ultrasonography processor 106 for producing typical US images. That is, images in which the structure or architecture of the patient by analyzing the strength and time elapsed for an echo of sound pulses directed into the patient. However, the US imaging component 104 can further include a sonoelastography processor 108 and a Doppler image processor 110. The sonoelastography processor 108 can be configured to analyze shear waves generated in a patient and estimate tissue modulus, i.e., tissue stiffness.

One of the most important characteristics of tissue performance is its elasticity. An appropriately elastic or supple tissue will perform optimally, while one which is not sufficiently elastic (e.g., stiff or rigid tissues) will offer reduced performance. The elastic modulus is not something that can be seen with normal ultrasound. Sonoelastography enables the measurement of tissue modulus, giving a better indication of tissue dysfunction than a visual image.

The Doppler image processor 110 can be configured to utilize color, power, or spectral Doppler analysis of Doppler measurements to see and evaluate blood flow. In the various embodiments, all three processors can be concurrently used to generate images that thus represent structure, stiffness, and blood flow in soft tissues.

As shown in FIG. 1, the transducer 112 and electrodes 114 are incorporated into a single head unit 111 coupled to the components in housing via, for example, wiring or cabling. Thus, the same head unit can be utilized to perform imaging plus the subsequent electrical stimulation treatment. Such a configuration is advantageous if the clinician believes there is dysfunctional tissue, i.e. a muscle tear or strain, at the site where pain is felt by the patient in that is unnecessary to use the electrodes 114 to search for the muscle tear or strain after the transducer 112 is utilized to locate a location for treatment in the patient. In particular, the electrodes are "pre-positioned" and electrical stimulation treatment can be immediately applied. Further, since no repositioning is needed, the electrical stimulation treatment can be applied more accurately. Finally, since no repositioning is needed, the area of interest can be immediately reevaluated using the transducer 112 and additional treatments can be provided without the need to reposition the head unit 111 on the patient.

Alternatively, this same type of confirmation is advantageous if Neuromuscular Interactive Stimulation is used to locate dysfunctional tissue. In such a configuration, since there is direct feedback from the patient once the area with dysfunctional tissue is located, it does not require special skills to identify the dysfunctional tissues via US. As a result, an area of dysfunctional tissue may be found more quickly. Further, since the transducer 112 is collocated, the transducer 112 can be immediately applied to verify or more closely examine the dysfunctional tissues without needing to reposition the head unit on the patient 111.

The same head unit shown in FIG. 1 can also be utilized to use electrical stimulation to locate areas of dysfunctional tissue that exists at distances away from where the patient feels pain, and then the same head is used to perform imaging plus the subsequent electrical stimulation treatment. Such a configuration is advantageous when the clinician desires to search for dysfunctional tissue that exists away from where pain is felt by the patient, in that it is unnecessary to position the transducer 112 after the electrodes 114 are utilized to locate a location for treatment in the patient. Rather, the transducer is "pre-positioned" and ultrasound imaging can immediately be performed followed by electrical stimulation treatment. Further, since no repositioning is needed, the ultrasound imaging can be performed quicker and more accurately since less areas needs to be scanned using the transducer. Finally, since no repositioning is needed, the area of interest can be immediately reevaluated and additional treatments can be provided without the need to reposition the head unit 111 on the patient.

Additionally, in some configurations, the system 100 can incorporate in housing 101 a vibrational waveform generating component 103 and a vibrational transducer 113 device coupled thereto for generating the shear waves needed for sonoelastography. The transducer 112 can then detect the shear waves. The component 103 can be configured for generated low frequency waves (~1-10 kHz). In some configurations, as shown in FIG. 1, the vibrational transducer 113 can be a separate device from head unit 111. This allows the shear waves to be introduced into the patient at different points of the patient's body, which may be necessary depending on the suspected location of injury. However, as also shown in FIG. 1, the vibrational transducer 113 could also be incorporated into head unit 111. The system of FIG. 1 can perform the sonoelastography in a variety of modes. One mode of operation of sonoelastography is discussed, at least in part, by Bharat and Varghese in "Radiofrequency electrode vibration-induced shear wave imaging for tissue modulus estimation: A simulation study." The Journal of the Acoustical Society of America. 2010; 128(4):1582-1585. doi:10.1121/1.3466880, the contents of which are hereby incorporated by reference in their entirety.

In addition to the foregoing components, system 100 can also include in housing 101 a controller 116 for coordinating and controlling operations of the e-stim component 102 and the US imaging component 104. The housing 101 can also include a display 118 for displaying images and other information to users. Although shown in FIG. 1 as being directly connected to the controller, the display can be concurrently or alternatively coupled to the US imaging component 104. The system can also include a user interface 120 with human interface elements (not shown) such as a keyboard or keypad, a pointing selection device, a touchscreen, or any other elements suitable for providing user input to controller 116 for controlling the various components of system 100. However, in some implementations, the user interface for system 100 can be a separate computer, tablet, or smartphone in communication with system 100.

In FIG. 1, system 100 is illustrated using a particular combination of components in housing 101. However, in the various embodiments, the system 100 can be implemented using more or less components than shown in FIG. 1 while achieving the same functionality.

As noted above, the system 100 includes a head unit 111 with at least the transducer 112 for US imaging and the electrodes 114 for electrical stimulation treatment. Thus, the head unit 111 and system 100 can be configured in a variety of ways. Two examples are illustrated in FIGS. 2 and 3.

Figure 2A:
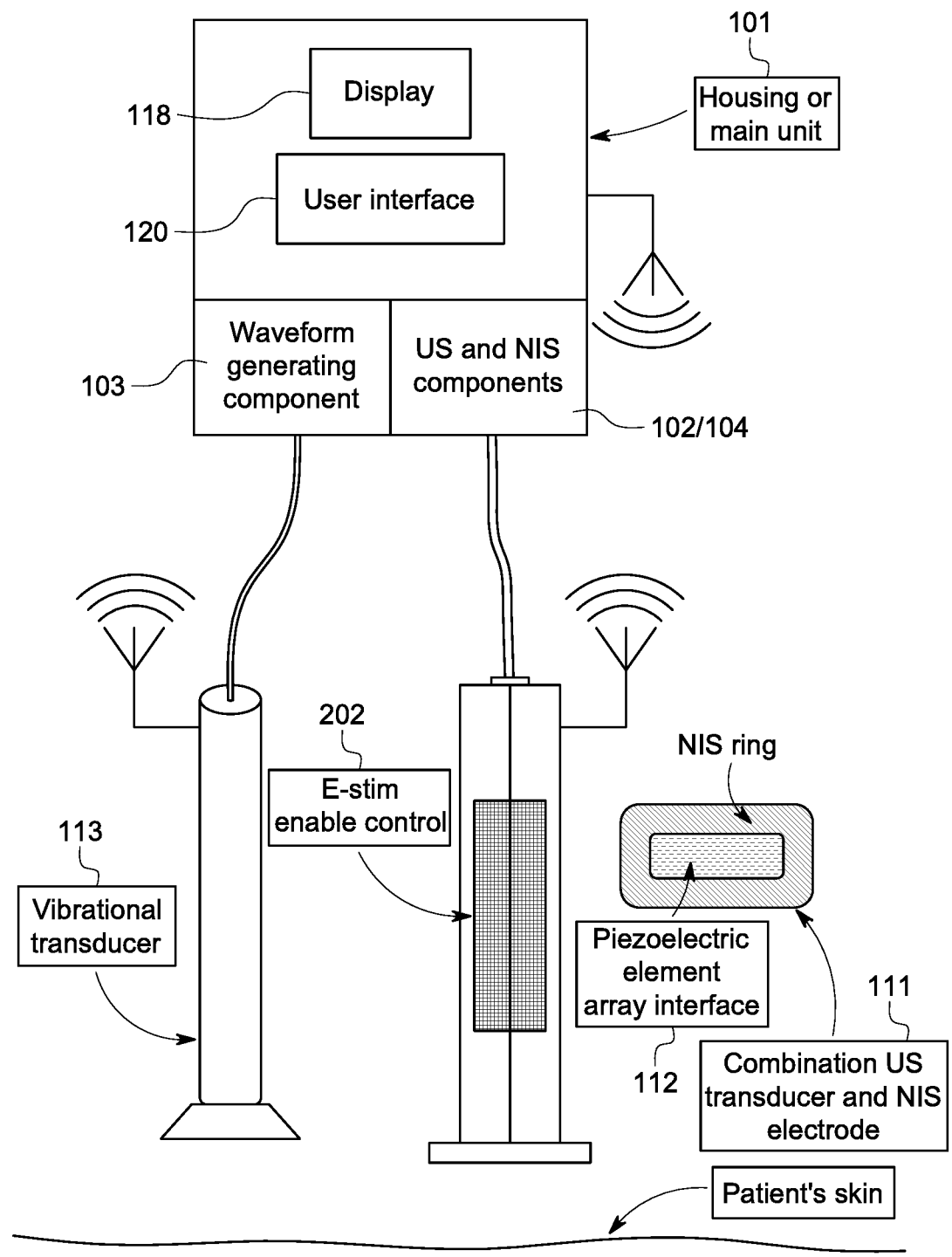
FIGS. 2A-2C show some exemplary configurations for the system of FIG. 1.

Turning first to FIG. 2A, there is shown a first exemplary configuration for the system of FIG. 1. As in FIG. 1, the configuration of FIG. 2A provides a housing 101 for components 102, 103, and 104, as well as having a display 118 and a user interface 120. As also shown in FIG. 1, the configuration of FIG. 2 also includes a head unit 111 and a separate vibrational transducer 113, coupled by wiring or cabling to the appropriate components in housing 101.

The head unit 111 is configured to support both US imaging and electrical stimulation treatment in a compact unit that is easy to use. For example, the head unit 111 can include, as shown in FIG. 2A, an enable button 202 to active electrical stimulation. In operation, the system can be configured for US imaging by default and the head unit 111 can be moved over the patient until a region of interest (i.e., the region to be treated) is located via the US imaging. Then, while visualizing the region of interest, the enable button 202 can be activated to cause the electrical stimulation to be applied. When deactivated, the head unit can resume imaging. In some configurations, switching between US imaging and electrical stimulation can be completely automated. In other configurations, user intervention or control can be required.

Additionally, as shown in the inset of FIG. 2A, both the transducer 112 for US imaging and the electrodes 114 for electrical stimulation treatment can be incorporated into the same face 204 of head unit 111. The arrangement of transducer 112 and electrodes can vary in the various embodiments. However, in particular embodiments, a ring-type structure can be used. That is, a central portion of the face 204 can include the transducer 112, such as in the form of a piezo-electric element array. This central portion can then be surrounded by an electrode 114 in the form of an electrical stimulation ring. However, the various embodiments are not limited to this design and any arrangement of transducers and electrodes can be used in the various embodiments.

Figure 2B:
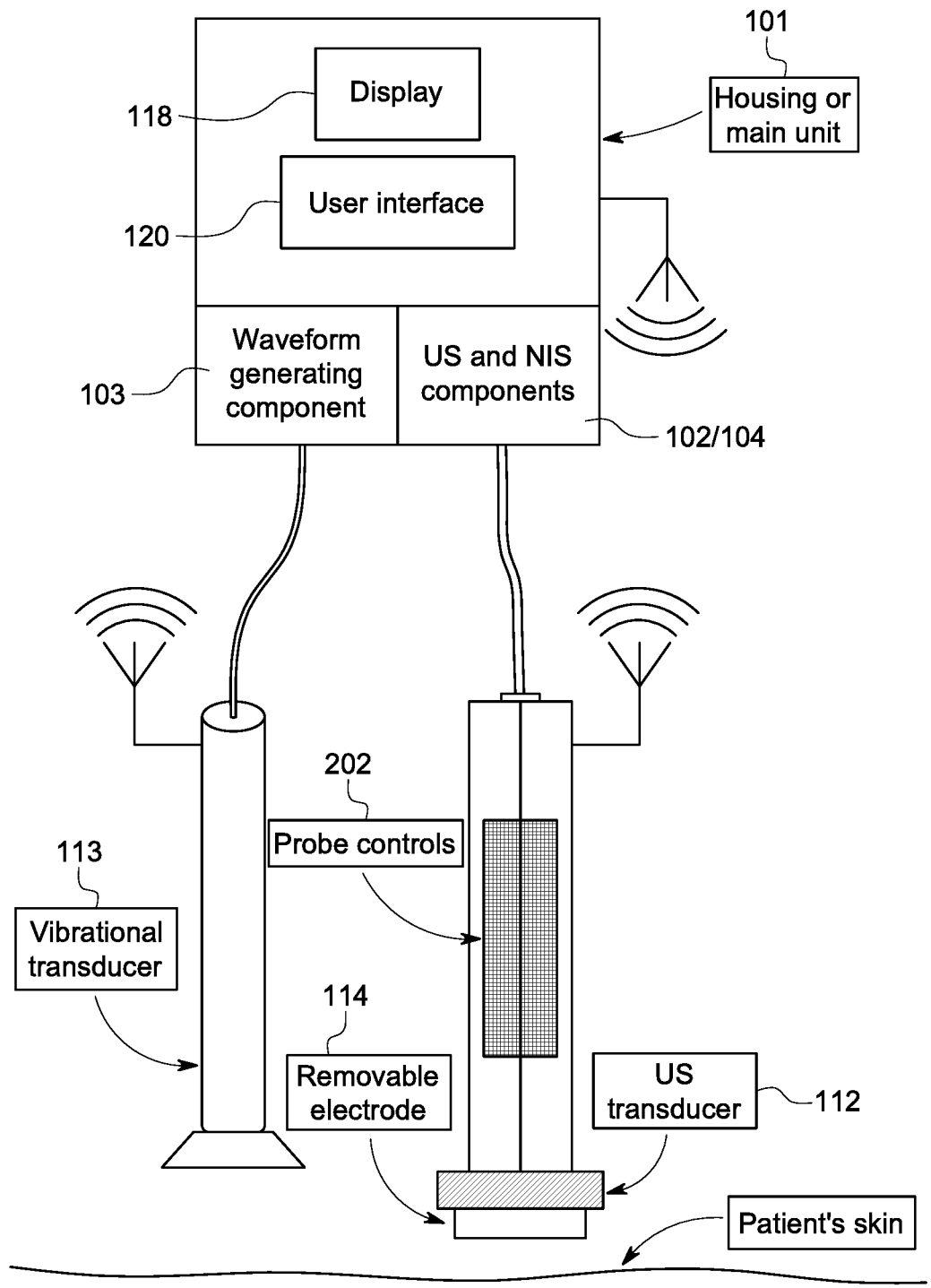
Figure 2C:
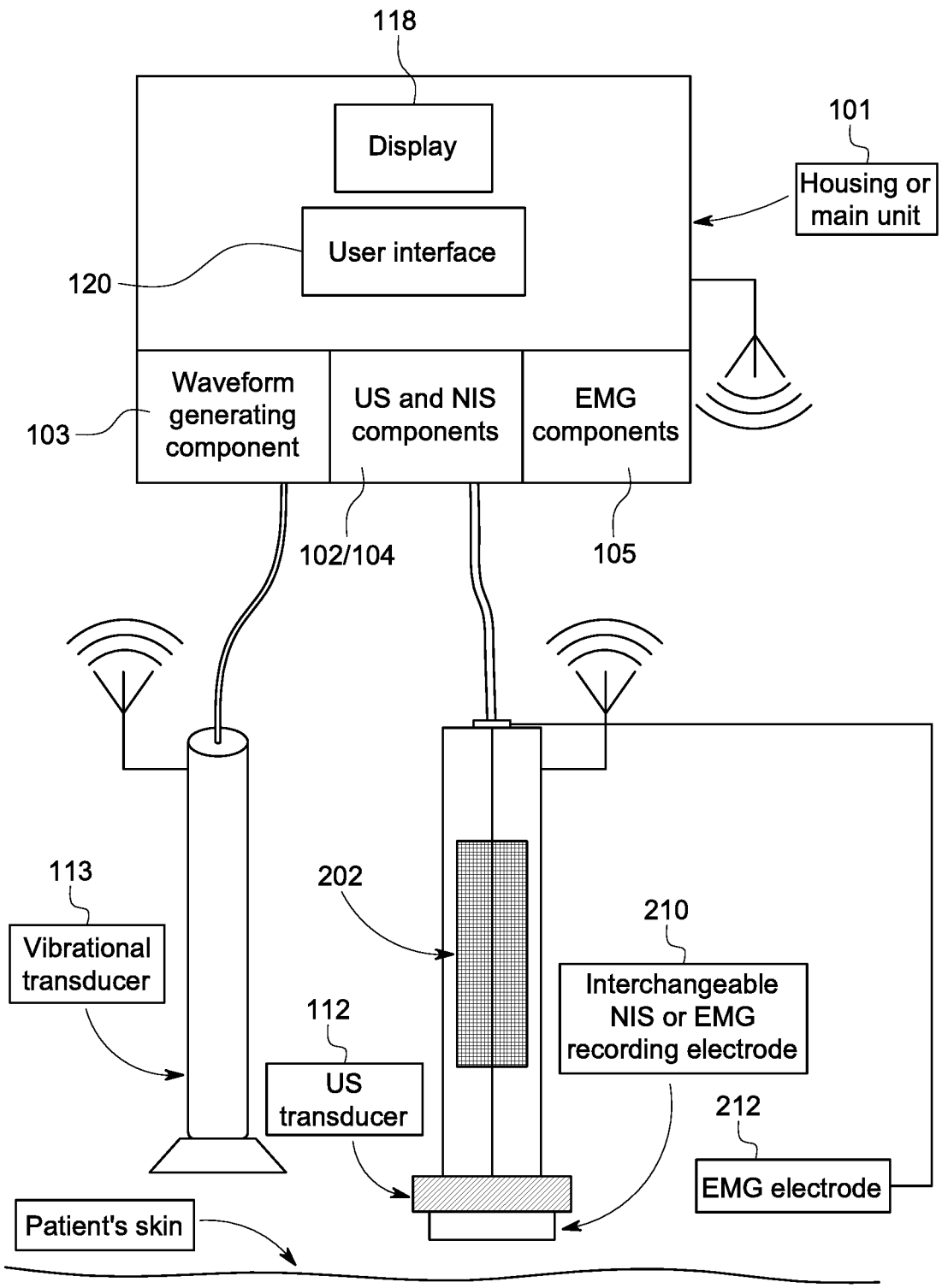

Variations on the arrangement of FIG. 2A are possible to provide additional functionality. For example, FIG. 2B shows a similar arrangement to that of FIG. 2A. However, in FIG. 2B, removable electrode is provided. This type of arrangement is discussed below in greater detail with respect to FIGS. 4A-4C. FIG. 2C shows yet another arrangement similar to that of FIG. 2A. In FIG. 2C, housing 101 also contains components 105 for supporting electromyography (EMG).

As used herein, EMG refers to the electrodiagnostic medicine technique for evaluating and recording the electrical activity produced by skeletal muscles. Component 105 can be an instrument called an electromyograph to produce a record called an electromyogram. The electromyograph detects, via the EMG electrodes attached thereto, the electric potential generated by muscle cells when these cells are electrically or neurologically activated.

Thus, one or more EMG electrodes 212 can be coupled to the EMG components 105. In such configurations, these can be one or more EMG percutaneous recording needle electrodes, one or more EMG surface recording electrodes, one or more EMG transcutaneous stimulation electrodes, or a combination of these. In these configurations, the EMG electrodes can be controlled from the main unit 101 or from controls 202 in the head unit 111.

It should be noted that in the various embodiments in which controls are included in a probe or head unit 111, such controls can be used to adjust and control a variety of settings. These include, but are not limited to, gain or depth adjustment for the US transducer 112 control of frequency, power and polarity adjustment for e-stim and, sound, volume, protocol and mode adjustment/selection for EMG operations.

Figure 3A:
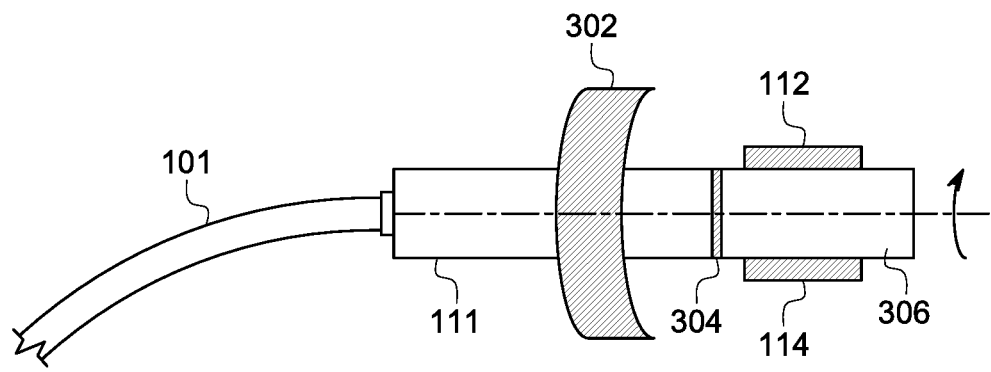
FIG. 3A-3I show other exemplary configurations for the system of FIG. 1.

Turning next to FIG. 3A, there is shown another exemplary configuration for the system of FIG. 1. In particular, FIG. 3A shows an implementation of head unit 111. Like head unit 111 in FIG. 1, head unit 111 in FIG. 3A also includes a transducer 112 for US imaging and electrodes 114 for providing electrical stimulation. However, as shown in FIG. 3A, head unit can be configured to include a flexible wrap or strap 302, a swivel 304, and a rotatable end portion 306. The use and operation of these components is illustrated in FIGS. 3B, 3C, and 3D.

Figure 3B:
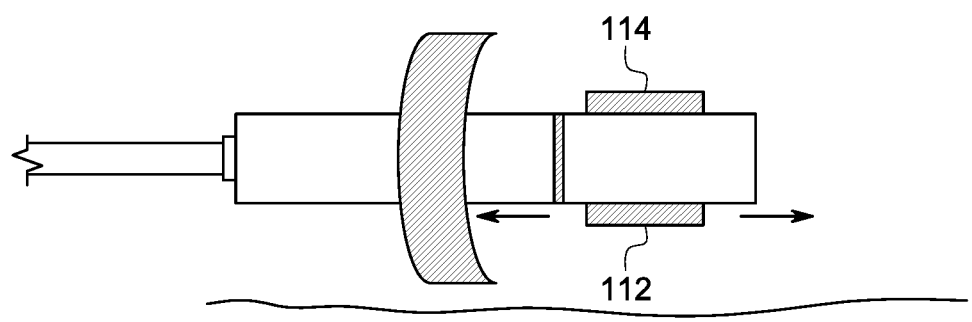
Figure 3C:
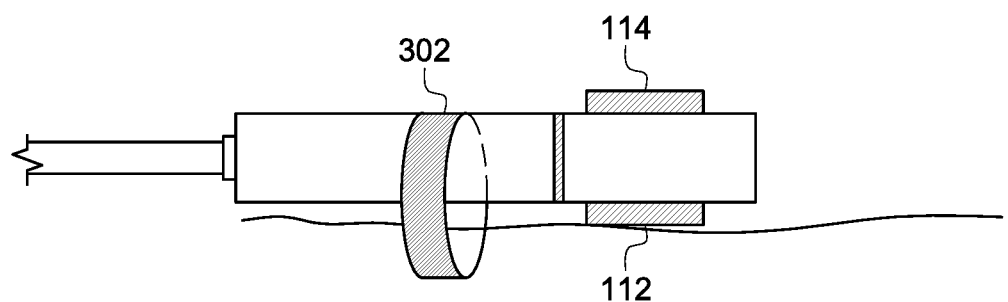
Figure 3D:
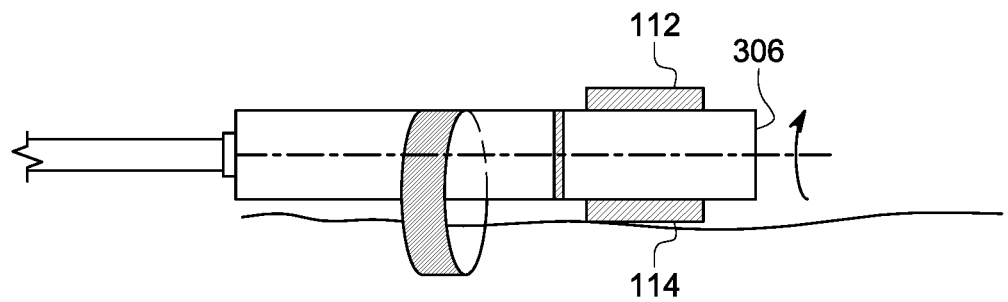

First, as shown in FIG. 3B, the head unit 111 is positioned over a patient so that the US transducer 112 is positioned for imaging and to allow the head unit 111 to be moved over the surface of the patient's skin to locate a region of interest. Next, as shown in FIG. 3C, once a region of interest is identified, the strap 302 can be used to secure the head unit 111 in place. Thereafter, as shown in FIG. 3D, the rotatable end portion 306 can be rotated to provide the electrode 114 at the skin's surface. Finally, the electrical stimulation can be applied. If further US imaging and/or electrical stimulation is required, the rotatable head portion 306 can be alternated appropriately.

Figure 3E:
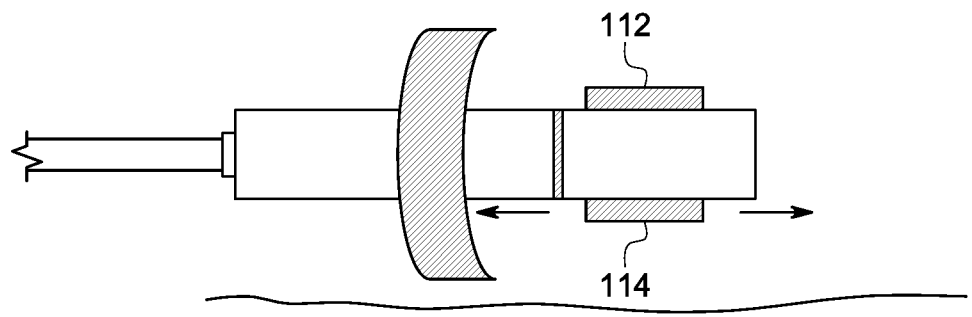
Figure 3F:
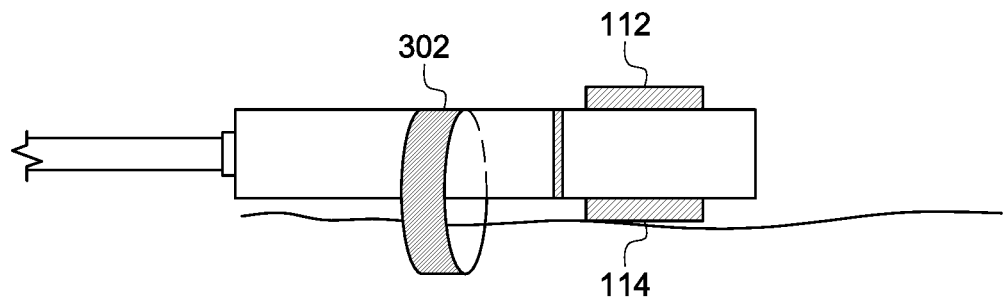
Figure 3G:
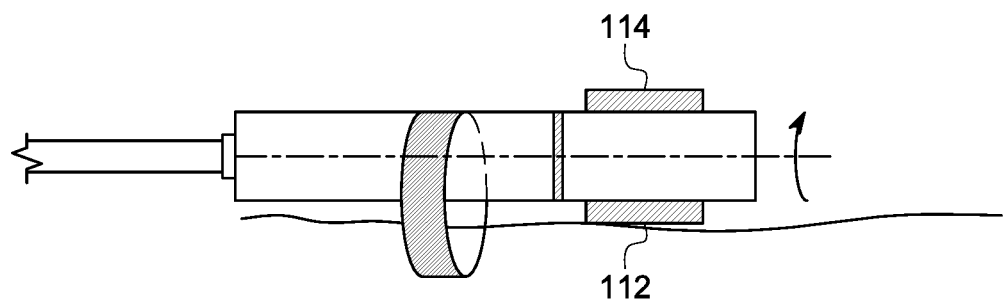
Figure 3H:
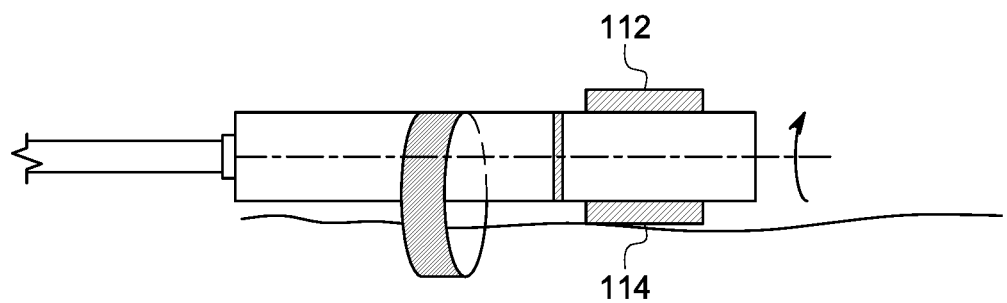

Alternatively, first, as shown in FIG. 3E, the head unit 111 is positioned over a patient so that the electrode 114 is positioned for scanning and to allow the head unit 111 to be moved over the surface of the patient's skin to locate a region of interest. Next, as shown in FIG. 3F, once a region of interest is identified, the strap 302 can be used to secure the head unit 111 in place. Next, as shown in FIG. 3G, the rotatable end portion 306 can be rotated to provide the US transducer 112 access to the skin's surface for visualization and measurement of the treatment area via ultrasound. Next, as shown in FIG. 3H, the rotatable end portion 306 can be rotated to provide the electrode 114 access to the patient's skin. Finally, the electrical stimulation can be applied. If further US imaging and/or electrical stimulation is required, the rotatable head portion 306 can be alternated appropriately.

It should be noted that rather than strap 302, any other means of securing the position of the head unit 111 relative to a patient can be used. For example, the head unit can be attached to a mechanical or robotic arm or other device that allows repositioning of the head unit 111 at a fixed location.

Figure 3I:
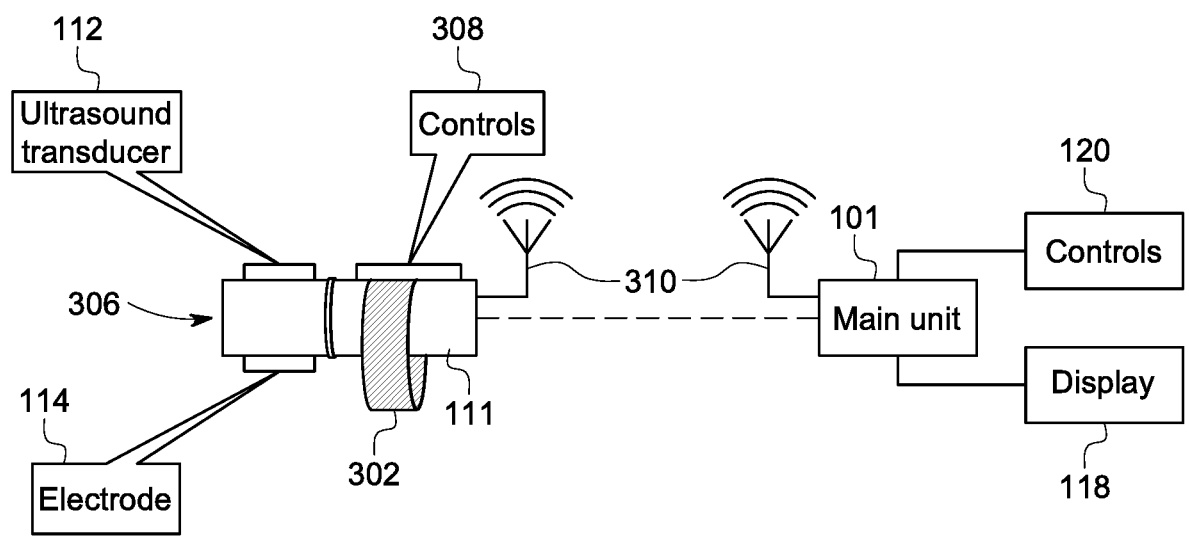

Although the configurations above show a wireline connection between head unit 111 and the main unit 101, in other configurations a wireless or a combination of wireless and wireline connections can be used. This is illustrated in FIG. 3I. As shown in FIG. 3I, the head unit 111 can communicate with main unit 101 via wireless links 310. Additionally, controls 308 can be provided at head unit 111 to improve usability when using wireless links 310. However, in some configurations, the head unit 111 can be controlled from main unit 101.

The configurations of FIG. 2 and FIG. 3A are presented solely as examples and for ease of illustration. Other configurations for head unit can be provided in the various embodiments. For example, such additional configurations are illustrated in FIGS. 4A-4C and 5.

Figure 4A:
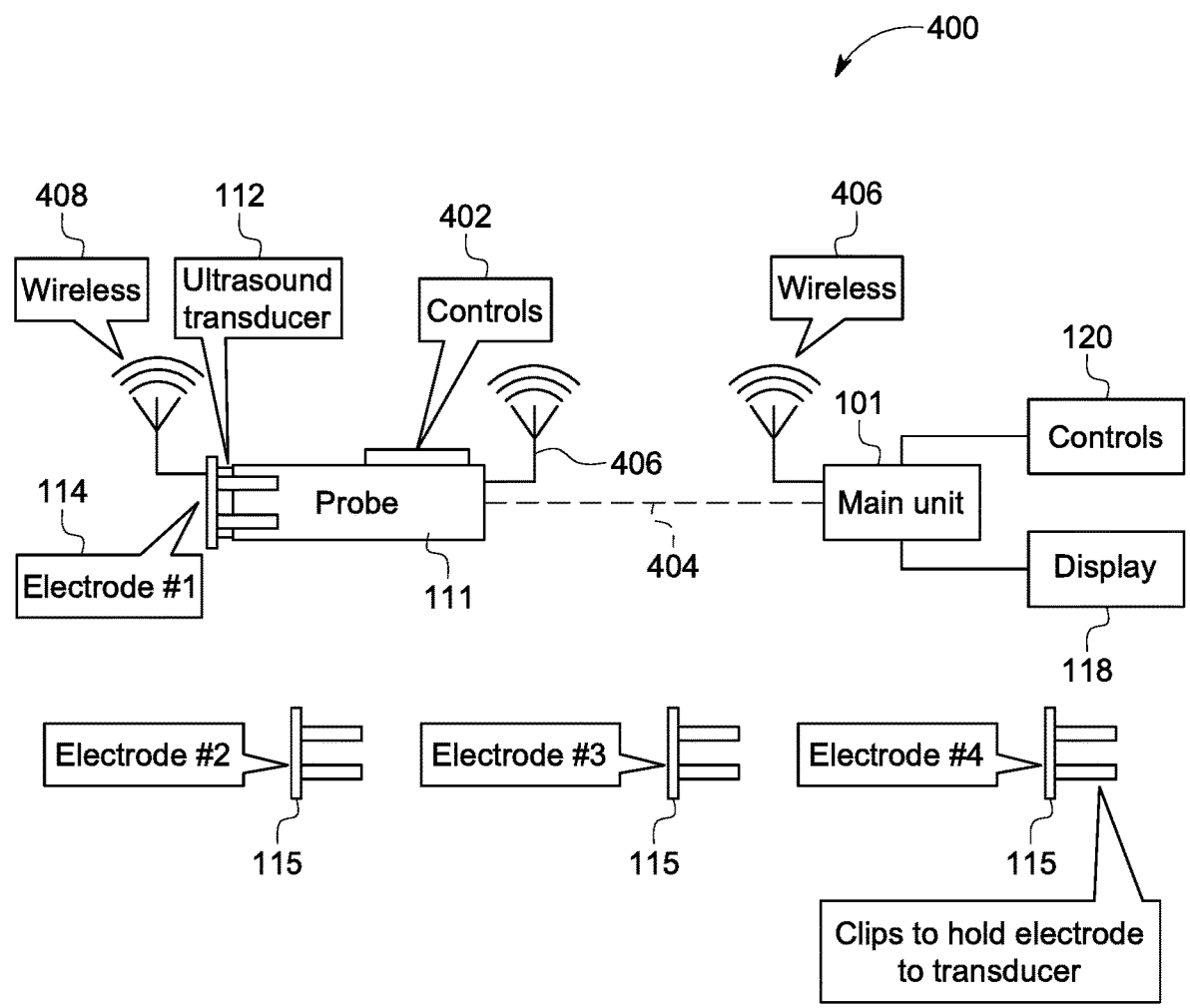
FIG. 4A-4C show other exemplary configurations for the system of FIG. 1.

Turning first to FIG. 4A, there is shown one exemplary configuration 400 for the system of FIG. 1. The configuration of FIG. 4A is similar to that of FIGS. 2 and 3A. Thus, the configuration 400 includes a probe or head unit 111, with a US transducer 112 and electrode(s) 114, which is coupled to a main unit or housing 101. The main unit 101 can include or be coupled to, as described above with respect to FIG. 1, controls or a user interface 120 and a display 118. The probe 111 can also include controls 402 for operating the system from the probe 111. The probe 111 and the main unit 101 can be communicatively coupled via a wireline communications link 404 or wireless communication links 406. The probe unit 111 can be powered via the main unit 101 in some configurations and powered independently in other configurations.

Figure 4B:
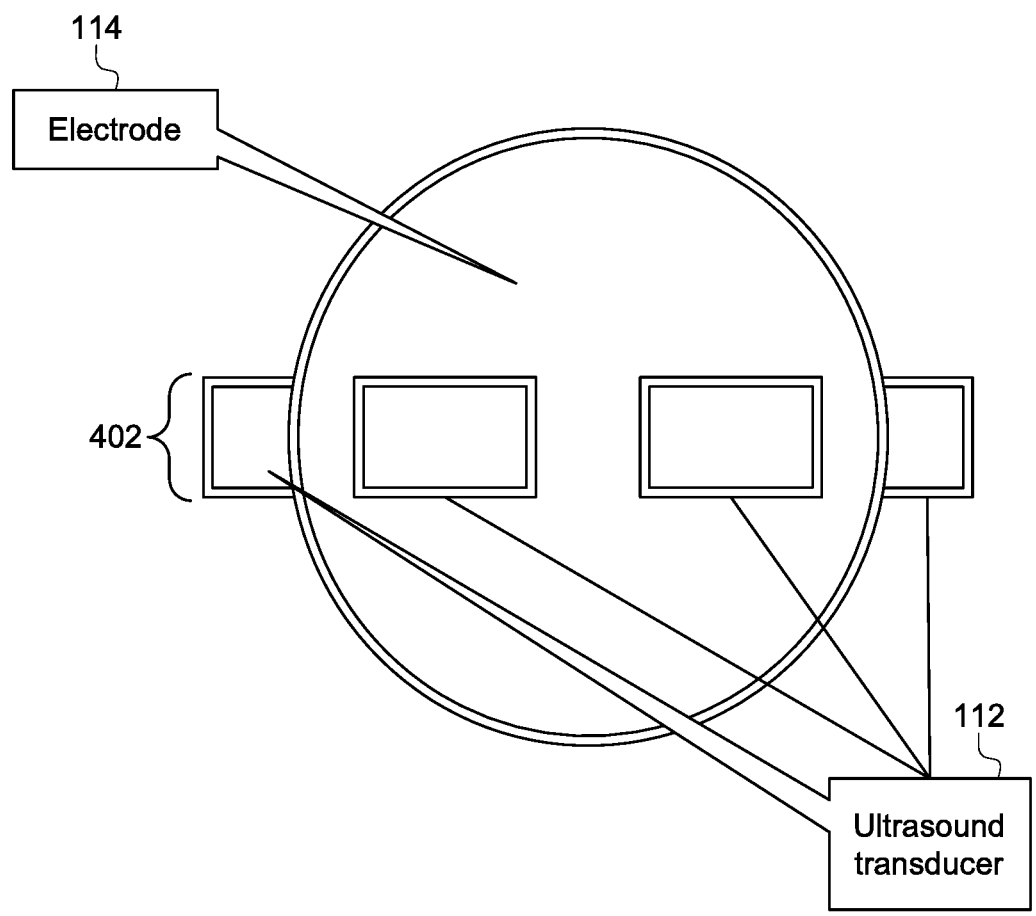

In the configuration of FIG. 4A, the US transducer 112 is located at one end of the probe 111 and the electrode 114 is placed over the US transducer 114. In such a configuration, the electrode 114 can be configured such that the US transducer 112 is accessible to provide and receive beams. For example as shown in FIG. 4B, the electrode 114 can be configured with one or more openings 502 to permit beams to propagate to and from the US transducer 112. It should be noted that while FIG. 4B shows one exemplary configuration for the electrode 114, the various embodiments are not limited in this regard. Rather, the electrode 114 can be configured in a variety of ways to permit propagation of the beams for the US transducer 112.

In some configurations, this arrangement of the US transducer 112 and the electrode 114 can be utilized to perform the methods described herein in substantially a similar fashion as described above with respect to FIGS. 2 and 3A-3H.

In other configurations, the arrangement in FIG. 4B can be configured to perform a proper placement of multiple electrodes prior to treatment. That is, the electrode 114 can be removable coupled to the probe 111, mechanically and electrically. This can be performed via one or more clips or other types of fasteners for establishing both mechanical and electrical connections. Thus, in accordance with the methods described above, the correct location for the electrode 114 on a patient can be identified and the electrode 114 can simply detach from the probe 111 to remain in place. Thereafter, another electrode 115 can be attached to the probe unit 111 and positioned on the patient as discussed above. This process can be repeated until all electrodes 114 and 115 are positioned. Finally, treatment can be provided.

Figure 4C:
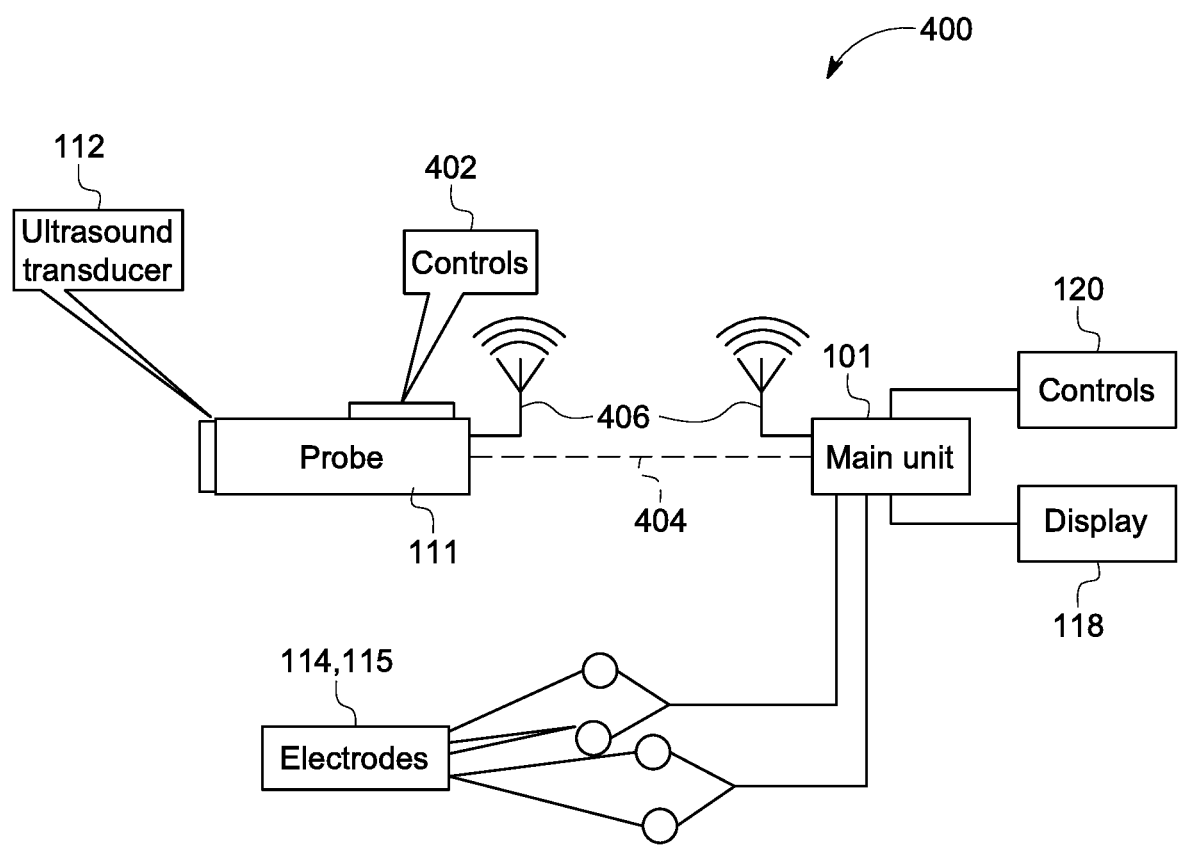

In such configurations, the electrodes 114 and 115 can be configured to operate via a wireless connection 408 to the main unit 101, as shown in FIG. 4A. Alternative, the electrodes 114, 115 can be coupled, for example, as shown in FIG. 4C to the main unit 101 via wireline connections.

It should be noted that the foregoing configurations are presented solely by way of example and not by way of limitation. Accordingly, systems in accordance with the various embodiments may include more or less components than shown above. For example, as shown above in some configurations, wireless or wireline connections are provided. However, wireline or wireless connections can be provided in any of the embodiments. In another example, some of the configurations above show the use of EMG components and electrodes. However, EMG components and electrodes can be provided in any of the embodiments.

Figure 5:
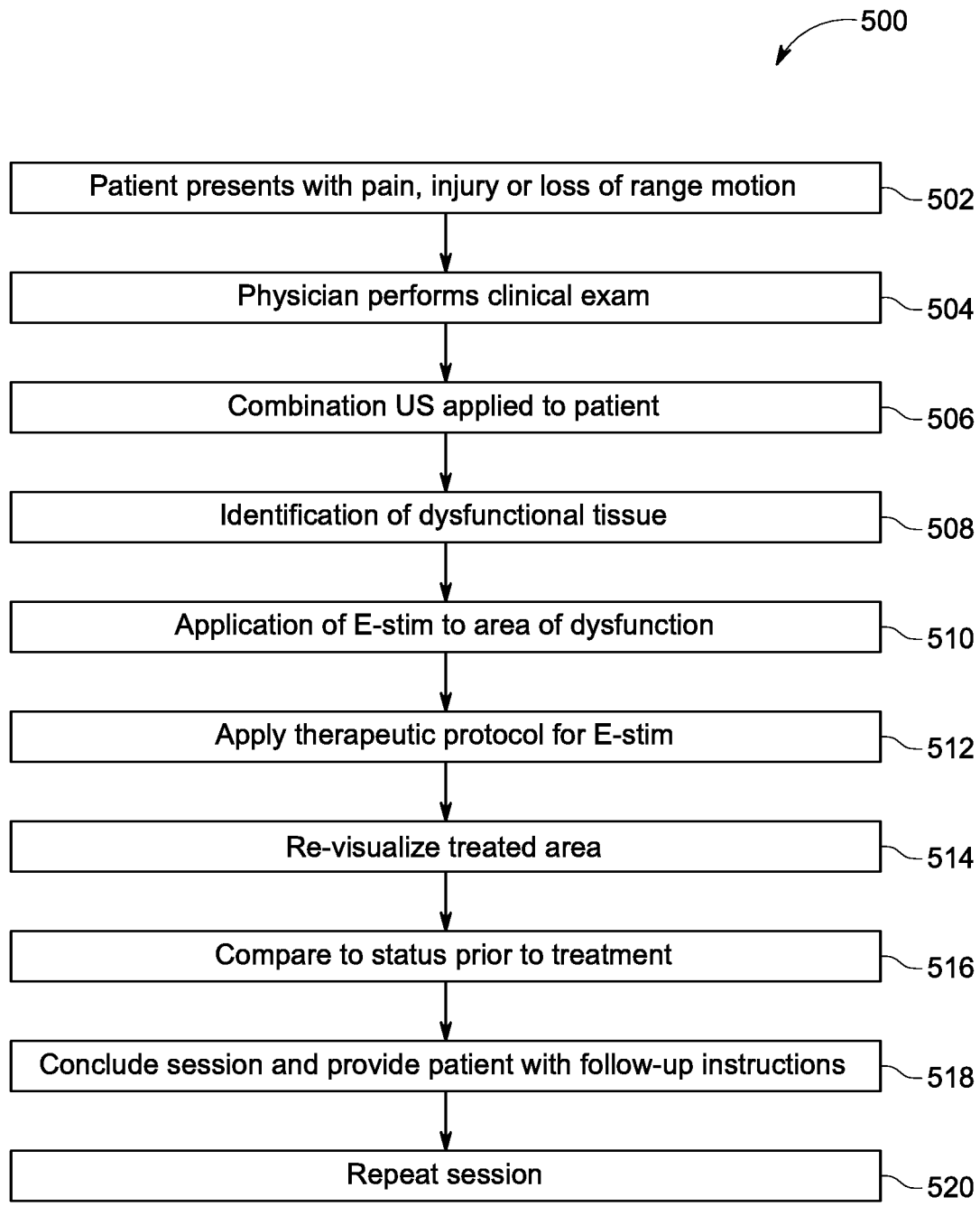
FIG. 5 is a flow chart of steps in a process for treating a patient in accordance with the various embodiments.

Having described various components of a system for implementing the methods of the various embodiments, attention is directed to FIGS. 5. 6, 7, 8, which discuss the methods of the various embodiments in greater detail.

Turning first to FIG. 5, there is shown a flowchart of steps in an exemplary procedure for treatment of dysfunctional tissues in a patient. The method begins at step 502 where a patient presents with some type of pain, injury, or loss or restricted range of motion. The physician or other healthcare worker can then perform a clinical examination at step 504 to determine presence or absence of dysfunctional tissue according to clinical criteria, apply pressure algometry to determine pain pressure threshold, and/or perform differential diagnosis for presence of dysfunctional tissue and to generally locate a location on the patient for treatment.

Thereafter, the method 500 can proceed to step 506, where the head unit 111 is positioned on the patient. If sonoelastography is also being performed, the vibrational transducer 113 is also positioned on the patient. The method of positioning the head unit 111 on the patient can depend on the clinical examination at step 504. This step can also involve the application of US liquid or gel to facilitate imaging.

Once the head unit 111 is positioned at step 506, the method can proceed to step 508. Step 508 first involves visualization of the dysfunctional tissue. Namely obtaining both structural and functional information. For example, using information gleaned from the US imaging (structural) and Doppler and/or sonoelastography analyses (functional), as described above with respect to FIG. 1, the precise location of the injury can be identified, as well as the type of injury. For example, the Doppler imaging will identify areas of unusual blood flow, the sonoelastography analysis will identify areas of unusual stiffness in muscle or other soft tissues, and the US imaging can be used to identify the locations of these, as well as identify any structural issues. In some implementations, the dysfunctional tissues can be identified automatically via software. In other implementations, the data is merely presented to the user and the user then reviews the data to identify the dysfunctional tissues.

In some configurations, electrical stimulation can be used at steps 506 and 508 to identify dysfunctional tissues. For example, as discussed above, Neuromuscular Interactive Stimulation can be used to identify the dysfunctional tissues. In such a configuration, electrical stimulation is provided via electrodes 114 and based on level of discomfort or pain produced by the electrical stimulation, one can identify the dysfunctional tissues, as discussed above.

After the dysfunctional tissues have been identified at step 508, the method can proceed to step 512. However, the method can optionally first proceed to step 510, where the electrodes for an e-stim component, such as electrodes 114 coupled to e-stim component 102 of system 100, are positioned appropriately for the dysfunctional tissues identified at step 508. For example, the electrodes 114 can be rotated into place, as discussed above with respect to FIGS. 3A-3D. Regardless, at step 512, electrical stimulation is provided via an appropriate treatment protocol.

In some configurations, the appropriate treatment protocol can be automatically selected by the system 100 based on the results of step 508. In other configurations, the system can provide one or more recommendations for the appropriate treatment protocol. However, the user ultimately selects one for actual use.

Once the treatment at step 512 is complete, the method can proceed to step 514. There, the area of treatment is re-visualized. This can involve repeating step 506 and 508 as needed. Thereafter, based on the information gleaned from the revisualization at step 514, the effectiveness of treatment can be evaluated at step 516. In particular, the information, before and after treatment, can be compared to determine if treatment was effective. In some implementations, the evaluation can be performed automatically via software. In other implementations, the data is merely presented to the user and the user then reviews the data to evaluate the results of the treatment.

After the evaluation, the method 500 can proceed in various ways. For example, the method can proceed to step 518, where the treatment session is concluded. At this point, the patient can be provided instructions, including instructions for further treatment. Alternatively, at step 520, a treatment session is immediately repeated, possibly multiple times. Regardless of the scheduling of the treatment sessions, they can be repeated until the dysfunctional tissue is reduced or eradicated, until pain is eliminated, until the injury is healed, or until normal function and/or range of motion is restored.

In some configurations, the determination that additional treatment is needed can be performed automatically. That is, if the comparison at step 516 does not indicate a sufficient change in structure or function or fails to meet any other criteria, the system 100 can be configured to automatically restart treatment. The treatment can continue until the criteria for discontinuing treatment is met. Such criteria can also involve halting treatment to avoid excessive treatment of the patient.

Figure 6:
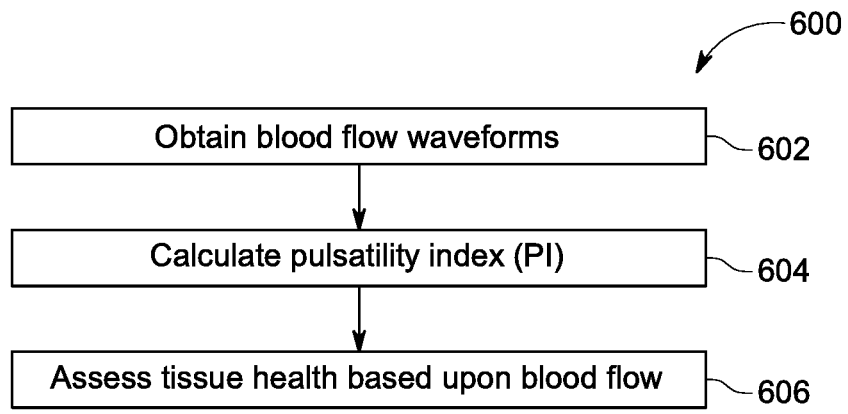
FIG. 6 is a flow chart illustrating a Doppler analysis according to the various embodiments.

As discussed above, step 508 involves visualization and identification of dysfunctional tissue using sonoelastography and Doppler analyses. These processes are described with respect to FIGS. 6 and 7. FIG. 6 schematically outlines the steps for Doppler analysis 600 and FIG. 7 schematically outlines the steps for sonoelastography analysis 700.

As shown in FIG. 6, the Doppler analysis 600 first involves obtaining blood flow waveforms at step 602. Doppler imaging has been used to assess blood flow in the neighborhood of myofascial trigger points (MTrPs) yielding blood flow scores of the vascular bed and adjacent soft tissue that effectively distinguish MTrPs. E.g. a constricted vascular bed and an enlarged vascular volume can be explained by observed flow waveforms with retrograde diastolic flow. Next, at step 604, the blood flow waveforms are utilized to calculate a pulsality index (PI) for the area being imaged. In some implementations, software can be provided to collect data, interpret and provide the PI result. PI=[PSV−MDV]/mean velocity, where PSV is peak systolic velocity and MDV is minimum diastolic velocity. Finally, based on the calculated pulsality index, an assessment of the health of the area being imaged. In some implementations, the calculations and evaluation of health can be performed automatically via software. For example, software can assign a blood flow waveform score (BFS) based upon a range from normal arterial flow to abnormal high resistance flow with retrograde diastolic flow. In other implementations, the data is merely presented to the user and the user then reviews the data to determine health.

Figure 7:
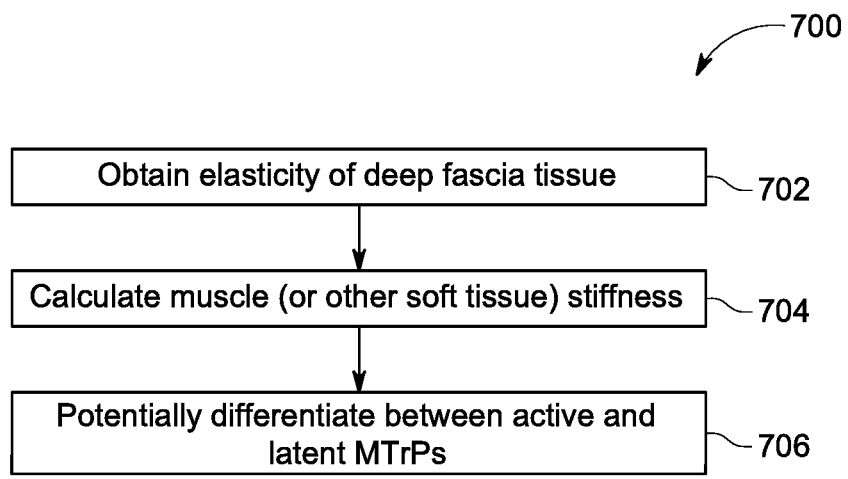
FIG. 7 is a flow chart illustrating a sonoelastography analysis according to the various embodiments.

As shown in FIG. 7, the sonoelastography analysis 700 begins at step 702 by obtaining elasticity data for deep fascia tissues. This can involve generating low frequency (<1000 Hz) shear waves from an external source (or possibly by the e-stim device). The waves are generated so that they propagate through the region of interest and their peak vibration amplitude is evaluated to obtain elasticity data. Thereafter, based on this elasticity data, the stiffness of muscles and other soft tissues in the imaged area can be calculated at step 704. Finally, based on the calculated stiffness, areas of nodules can be calculated and used to differentiate between active and latent MTrPs and thus identify or visualize areas for treatment.

The present disclosure contemplates that the systems and methods described herein can be used for a wide range of dysfunctions, and not solely active or latent MTrPs or other conditions explicitly specified herein. Reference to active or latent MTrPs or other express conditions is solely for ease of illustration and understanding.

Figure 8:
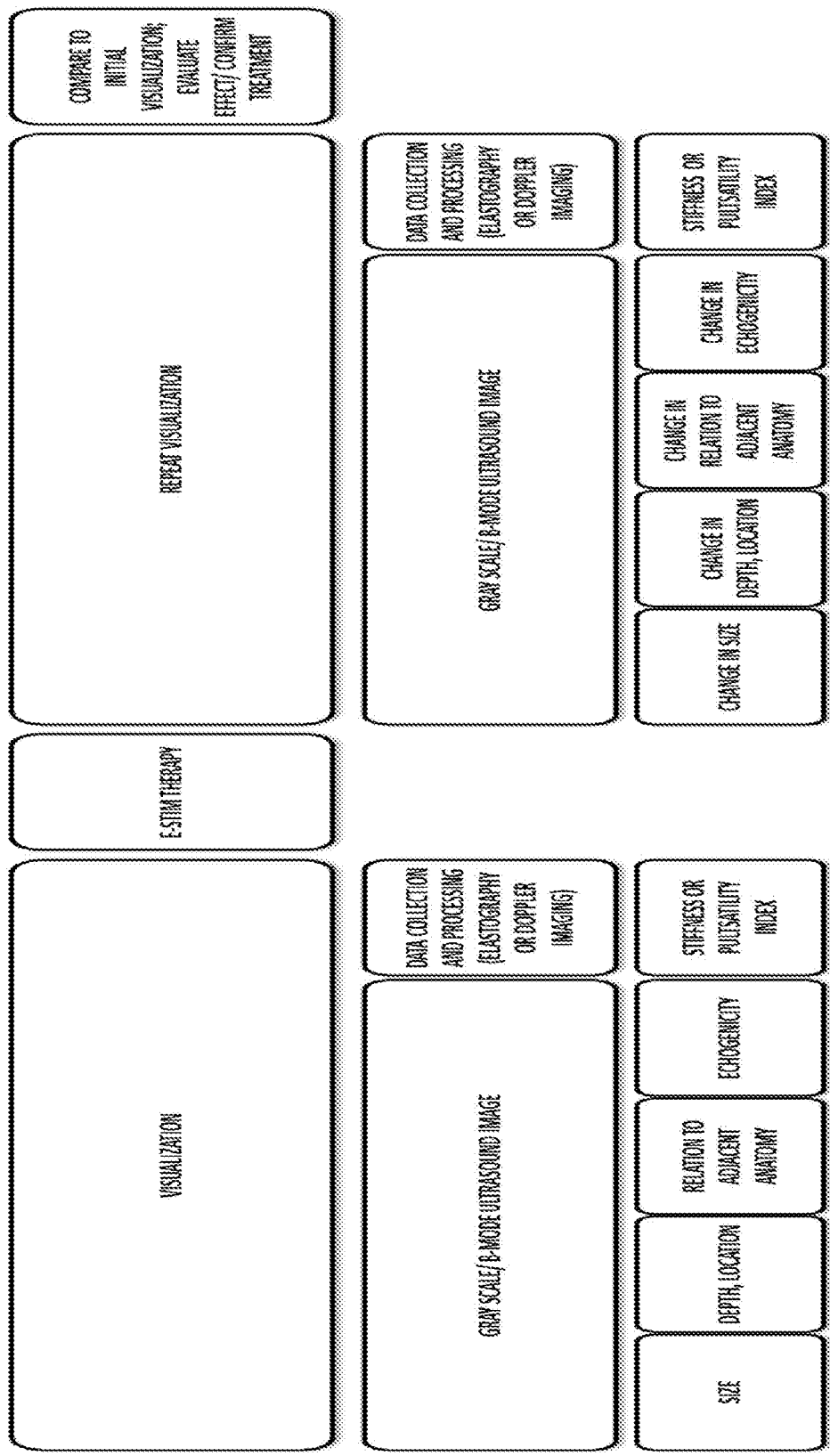
FIG. 8 is a schematic diagram of the processes and sub-processes involved in a method according to the various embodiments.

Although the procedure in FIG. 5 describes in general the treatment protocol/method of the various embodiments, FIG. 8 describes in greater detail operations at the various components of a system configured in accordance with the various embodiments.

FIG. 8 is a schematic of the sub-processes involved in the process of FIG. 7. Going left to right across the top row, the main sub-processes are identified. The second or middle row breaks down the main sub-processes, where appropriate further. The third or bottom row indicates the data obtain from the sub-processes.

The main sub-processes are as follows. First, a visualization sub-process is performed to identify and characterize the dysfunctional tissues. Next, e-stim therapy is performed according to the results of the visualization. Thereafter, the visualization is repeated. Finally, the initial and final results are compared to evaluate the effect of the e-stim treatment.

Each of the visualization and re-visualization sub-process involve, as discussed above, several imaging/analysis components, as shown in the middle row. The first component is the grayscale/B-mode imaging, as discuss above, to obtain structure information. As shown in the bottom row, this can involve obtaining size information, depth and location information, information regarding adjacent anatomy, and echogenicity. The second component is other data collection via Doppler analyses and/or sonoelastography analyses in order to obtain stiffness and/or pulsality index values. Optionally, as illustrated in FIG. 8, the data collected during the re-visualization can involve obtaining changes in values.

Figure 9:
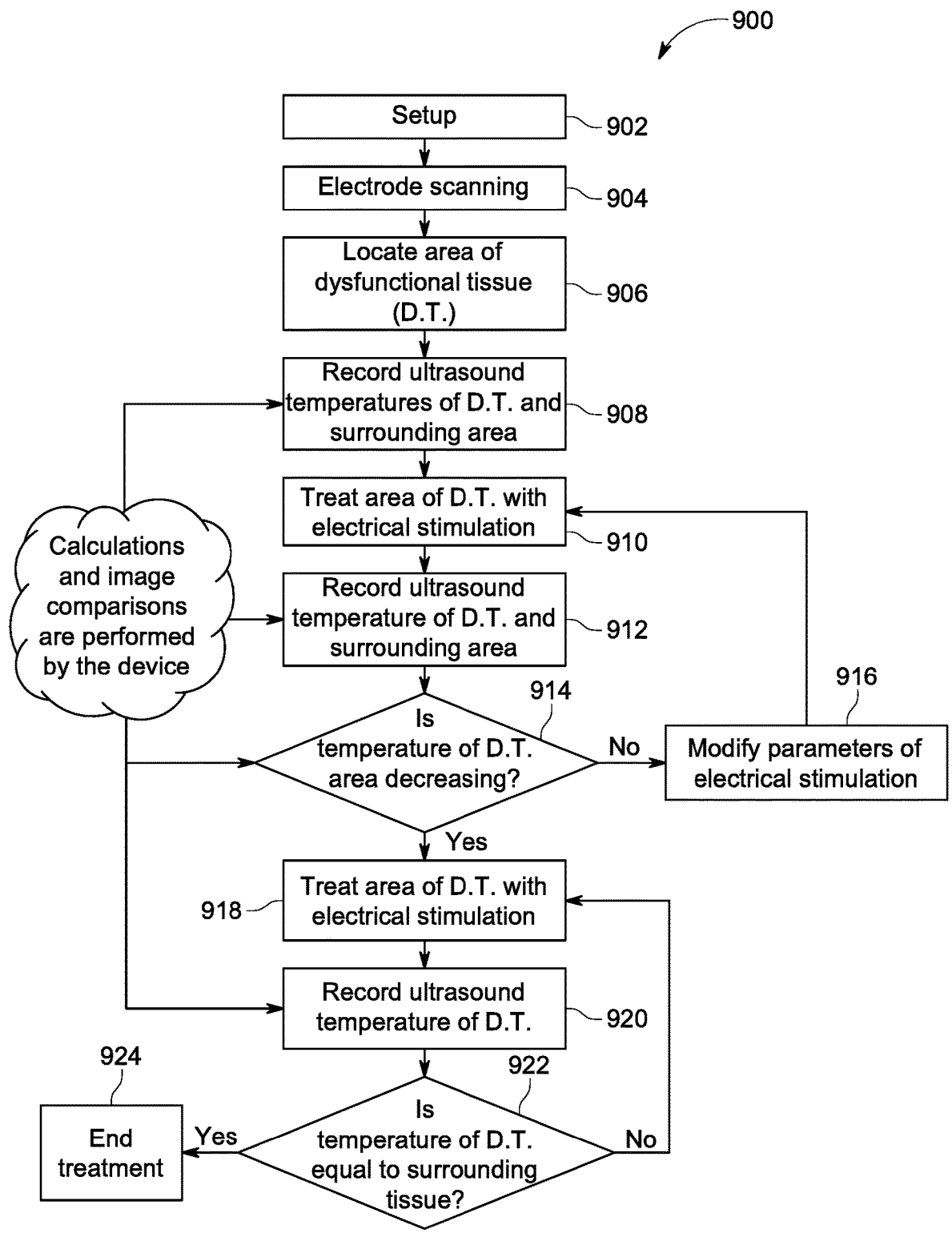
FIG. 9 is flow chart illustrating a treatment based on ultrasound temperature according to the various embodiments.

Now turning to FIG. 9, there is shown a flowchart of steps in an exemplary procedure for treatment of dysfunctional tissues in a patient based on monitoring of ultrasound temperature. Ultrasound temperature can be obtained in a variety of ways. One exemplary methodology for obtaining ultrasound temperature is described in U.S. Pat. No. 8,016,757, to Peter J. Kaczkowski and Ajay Anand, issued Sep. 13, 2011, the contents of which are hereby incorporated by reference in their entirety. However, the present disclosure contemplates that any other method for obtaining ultrasound temperature can be used in the various embodiments without limitation. The method 900 begins at step 902 with a setup of the system for scanning and treating a patient. After the system is setup, electrode scanning can be performed at step 904, as discussed above, until an area of dysfunctional tissue is located at step 906.

Once the area of dysfunctional tissue is located at step 906, the ultrasound temperatures of the dysfunctional tissue and the surrounding areas can be recorded at step 908. Thereafter, at step 910, the area with the dysfunctional tissue can be treated with e-stim. After the treatment at step 910, the ultrasound temperatures can again be recorded at step 912.

The method then moves on to step 914. At step 914, a determination is made as to whether a decrease in the temperature of the dysfunctional tissue is detected. If no decrease is detected, then the method proceeds to step 916, where the parameters for e-stim are modified. Thereafter, the method returns to step 910 for additional stimulation using the new parameters and the temperature is monitored at steps 912 and 914 until a temperature drop is detected. Once the temperature drop is detected at step 914, the method proceeds to step 918.

At step 918, further electrical stimulation can be provided. Thereafter, temperature is measured again at step 920. Thereafter, at step 922 it is determined whether the temperature of the dysfunctional tissue is equal to that of the surrounding tissue. If not, the method 900 repeats steps 918-922 until the temperature is equal. Once the temperature of the dysfunctional tissue is equal to that of the surrounding tissue, the method proceeds to step 924, where treatment is ended. In some configurations, if an increase in temperature is detected during steps 918-922, the method 900 can be configured to return to step 916, so that the parameters can be adjusted.

Figure 10:
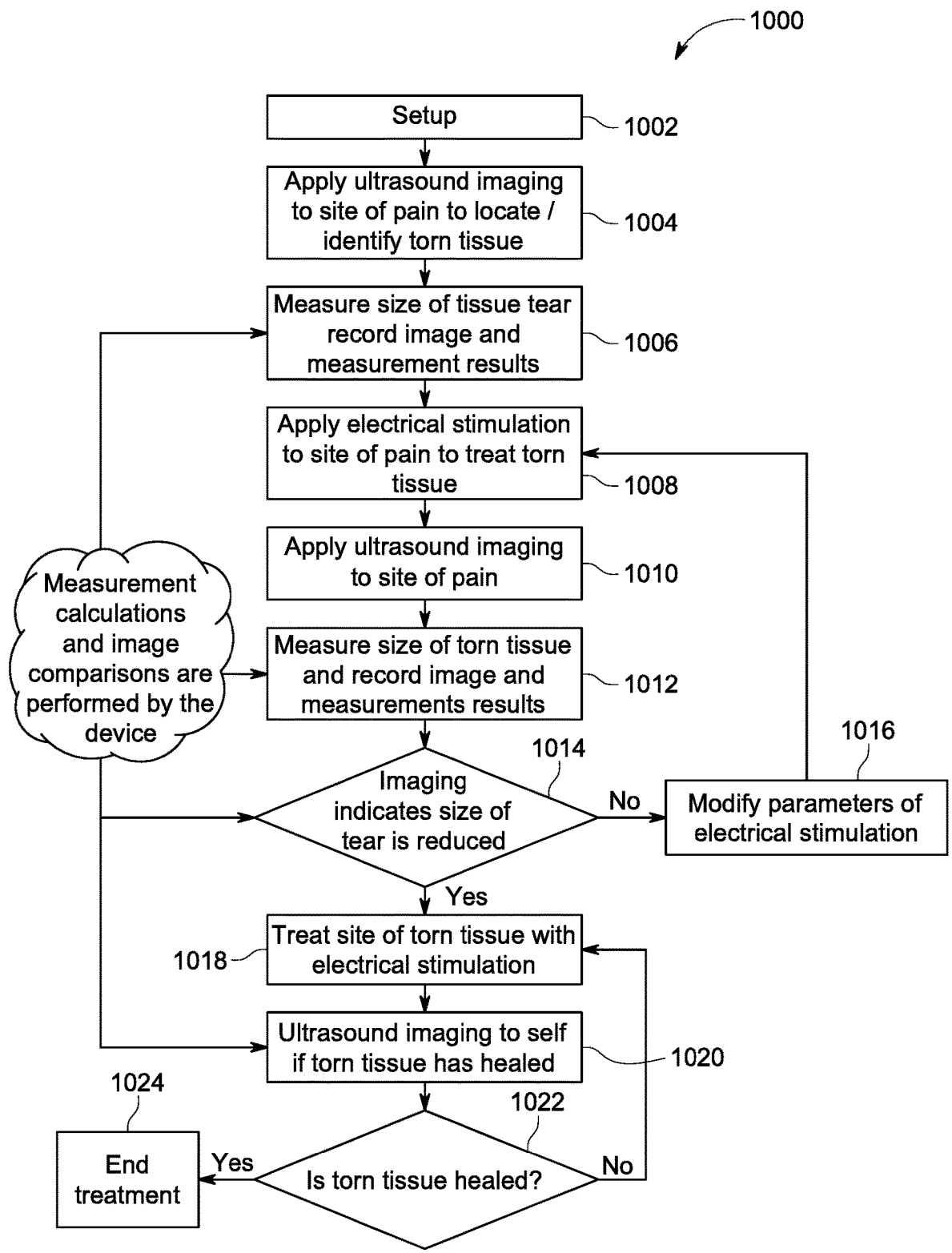
FIG. 10 is flow chart illustrating a treatment for torn tissues according to the various embodiments.

Now turning to FIG. 10, there is shown a flowchart of steps in an exemplary procedure for treatment of torn tissues in a patient based on monitoring of ultrasound imaging. The method 1000 begins at step 1002 with a setup of the system for scanning and treating a patient. After the system is setup, ultrasound imaging can be performed at step 1004 to identify and locate torn tissue in an area with pain. Thereafter, the size of the torn tissue and images of the torn tissue can be recorded at step 1006.

Once the area of torn tissue is located at step 1004 and measurements and images are obtained at step 1006, the area with the torn tissue (i.e., the area of pain) can be treated with e-stim. After the treatment at step 1010, additional images and measurements of the torn tissue can be recorded at step 1012.

The method then moves on to step 1014. At step 1014, a determination is made as to whether a decrease in the size of the tear is detected. If no decrease is detected, then the method proceeds to step 1016, where the parameters for e-stim are modified. Thereafter, treatment and monitoring are repeated with steps 1008-1016 until a decrease in the size of the tear is detected at step 1014. Once the decrease is detected at step 1014, the method proceeds to step 1018.

At step 1018, further treatment of the site is provided with the existing parameters. Thereafter, additional imaging is performed at step 1020 to determine if the torn tissue has been healed. If at step 1022, the tissue is not yet healed, the method can repeat steps 1018-1022 until healing is observed. Once the tissues are healed, the method can end at step 1024. In some configurations, if an increase in temperature is detected during steps 918-922, the method 900 can be configured to return to step 916, so that the parameters can be adjusted.

Figure 11A:
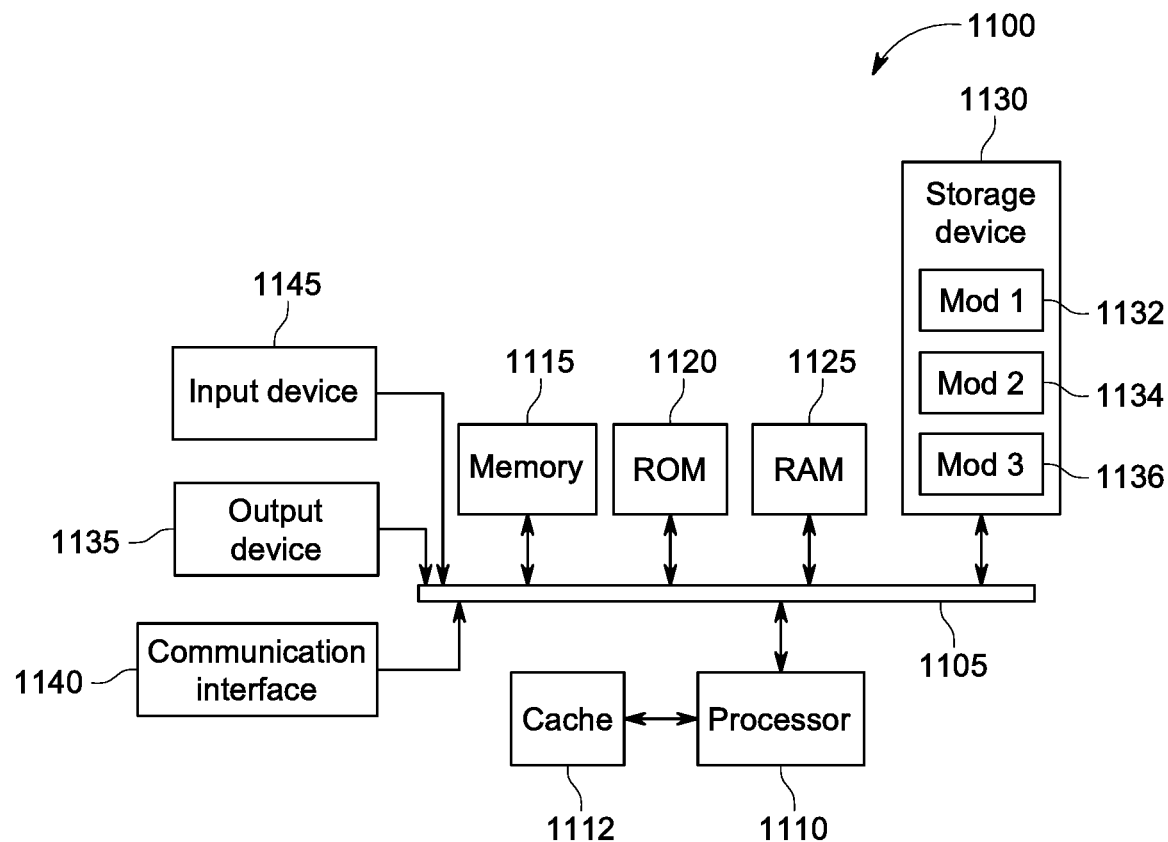
FIGS. 11A and 11B show a computing device that can be configured to implement the various embodiments.
Figure 11B:
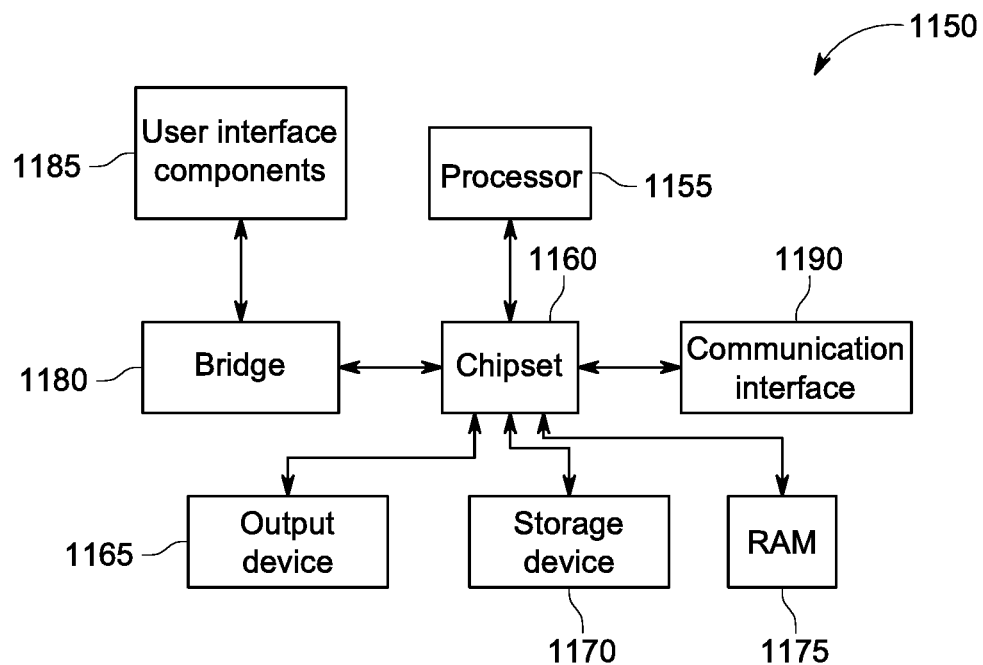

FIG. 11A, and FIG. 11B illustrate exemplary possible system embodiments. The more appropriate embodiment will be apparent to those of ordinary skill in the art when practicing the present technology. Persons of ordinary skill in the art will also readily appreciate that other system embodiments are possible.

FIG. 11A illustrates a conventional system bus computing system architecture 1100 wherein the components of the system are in electrical communication with each other using a bus 1105. Exemplary system 1100 includes a processing unit (CPU or processor) 1110 and a system bus 1105 that couples various system components including the system memory 1115, such as read only memory (ROM) 1120 and random access memory (RAM) 1125, to the processor 1110. The system 1100 can include a cache of high-speed memory connected directly with, in close proximity to, or integrated as part of the processor 1110. The system 1100 can copy data from the memory 1115 and/or the storage device 1130 to the cache 1112 for quick access by the processor 1110. In this way, the cache can provide a performance boost that avoids processor 1110 delays while waiting for data. These and other modules can control or be configured to control the processor 1110 to perform various actions. Other system memory 1115 may be available for use as well. The memory 1115 can include multiple different types of memory with different performance characteristics. The processor 1110 can include any general purpose processor and a hardware module or software module, such as module 1 1132, module 2 1134, and module 3 1136 stored in storage device 1130, configured to control the processor 1110 as well as a special-purpose processor where software instructions are incorporated into the actual processor design. The processor 1110 may essentially be a completely self-contained computing system, containing multiple cores or processors, a bus, memory controller, cache, etc. A multi-core processor may be symmetric or asymmetric.

To enable user interaction with the computing device 1100, an input device 1145 can represent any number of input mechanisms, such as a microphone for speech, a touch-sensitive screen for gesture or graphical input, keyboard, mouse, motion input, speech and so forth. An output device 1135 can also be one or more of a number of output mechanisms known to those of skill in the art. In some instances, multimodal systems can enable a user to provide multiple types of input to communicate with the computing device 1100. The communications interface 1140 can generally govern and manage the user input and system output. There is no restriction on operating on any particular hardware arrangement and therefore the basic features here may easily be substituted for improved hardware or firmware arrangements as they are developed.

Storage device 1130 is a non-volatile memory and can be a hard disk or other types of computer readable media which can store data that are accessible by a computer, such as magnetic cassettes, flash memory cards, solid state memory devices, digital versatile disks, cartridges, random access memories (RAMs) 1125, read only memory (ROM) 1120, and hybrids thereof.

The storage device 1130 can include software modules 1132, 1134, 1136 for controlling the processor 1110. Other hardware or software modules are contemplated. The storage device 1130 can be connected to the system bus 1105. In one aspect, a hardware module that performs a particular function can include the software component stored in a computer-readable medium in connection with the necessary hardware components, such as the processor 1110, bus 1105, display 1135, and so forth, to carry out the function.

FIG. 11B illustrates a computer system 1150 having a chipset architecture that can be used in executing the described method and generating and displaying a graphical user interface (GUI). Computer system 1150 is an example of computer hardware, software, and firmware that can be used to implement the disclosed technology. System 1150 can include a processor 1155, representative of any number of physically and/or logically distinct resources capable of executing software, firmware, and hardware configured to perform identified computations. Processor 1155 can communicate with a chipset 1160 that can control input to and output from processor 1155. In this example, chipset 1160 outputs information to output 1165, such as a display, and can read and write information to storage device 1170, which can include magnetic media, and solid state media, for example. Chipset 1160 can also read data from and write data to RAM 1175. A bridge 1180 for interfacing with a variety of user interface components 1185 can be provided for interfacing with chipset 1160. Such user interface components 1185 can include a keyboard, a microphone, touch detection and processing circuitry, a pointing device, such as a mouse, and so on. In general, inputs to system 1150 can come from any of a variety of sources, machine generated and/or human generated.

Chipset 1160 can also interface with one or more communication interfaces 1190 that can have different physical interfaces. Such communication interfaces can include interfaces for wired and wireless local area networks, for broadband wireless networks, as well as personal area networks.

Some applications of the methods for generating, displaying, and using the GUI disclosed herein can include receiving ordered datasets over the physical interface or be generated by the machine itself by processor 1155 analyzing data stored in storage 1170 or 1175. Further, the machine can receive inputs from a user via user interface components 1185 and execute appropriate functions, such as browsing functions by interpreting these inputs using processor 1155.

It can be appreciated that exemplary systems 1100 and 1150 can have more than one processor 1110 or be part of a group or cluster of computing devices networked together to provide greater processing capability.

For clarity of explanation, in some instances the present technology may be presented as including individual functional blocks including functional blocks comprising devices, device components, steps or routines in a method embodied in software, or combinations of hardware and software.

In some embodiments the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the above-described examples can be implemented using computer-executable instructions that are stored or otherwise available from computer readable media. Such instructions can comprise, for example, instructions and data which cause or otherwise configure a general purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can comprise hardware, firmware and/or software, and can take any of a variety of form factors. Typical examples of such form factors include laptops, smart phones, small form factor personal computers, personal digital assistants, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A non-invasive method for locating and diagnosing dysfunctional muscle tissues, and treatment of the dysfunctional muscle tissues, the method comprising:
   contacting a patient's skin with a head unit comprising a first face; the first face comprising both an electrode and an ultrasound transducer; the contacting step bringing both the ultrasound transducer and the electrode simultaneously into contact with the patient's skin in order to locate and diagnose a dysfunctional muscle tissue site in the patient, wherein the dysfunctional muscle tissue exhibits at least one symptom selected from the group consisting of injury, stiffness, pain, abnormal function, and range of motion;
   locating the dysfunctional muscle tissue site in the patient by neuromuscular interactive stimulation by moving the first face comprising both the electrode and ultrasound transducer over a portion of the patient's skin while applying an electrical stimulus from the electrode to the patient while the patient performs a body motion that engages suspected dysfunctional muscle tissues;
   discontinuing movement of the first face comprising both the electrode and ultrasound transducer and discontinuing the application of the electrical stimulus to the patient, while maintaining the first face over the located dysfunctional muscle tissue site;
   confirming the location of the dysfunctional muscle tissue site without further moving the first face comprising both the electrode and ultrasound transducer by electrically actuating the ultrasound transducer to obtain a first set of structural and functional information via a non-invasive ultrasound visualization process; and, thereafter, without moving the first face comprising both the ultrasound transducer and the electrode,
   transdermally applying an electrical stimulation treatment from the electrode to a portion of the patient's skin associated with the located dysfunctional muscle tissue site without moving the first face comprising both the electrode and ultrasound transducer;
   thereafter, obtaining a second set of structural and functional information for the region of interest in the patient via the non-invasive ultrasound visualization process; and
   evaluating an effect of the transdermally-applied electrical stimulation treatment based on a comparison of the first set of structural and functional information and the second set of structural and functional information.

2. The non-invasive method of claim 1, wherein the non-invasive visualization process comprises grayscale ultrasound imaging of the dysfunctional muscle tissue site and at least one of Doppler imaging of the dysfunctional muscle tissue site or sonoelastography of the dysfunctional muscle tissue site.

3. The non-invasive method of claim 1, wherein the first and second set of functional information comprises at least one of stiffness information for the dysfunctional muscle tissue site or blood flow information for the dysfunctional muscle tissue site.

4. The non-invasive method of claim 1, wherein the first and second set of structural information comprises at least one of size, depth, location, and echogenicity of the dysfunctional muscle tissue site, and location of anatomy adjacent to the dysfunctional muscle tissue site.

5. The non-invasive method of claim 1, wherein the electrical stimulation treatment is automatically selected based on the first set of structural and functional information.

6. The non-invasive method of claim 1, further comprising:
   determining that the effect of the electrical stimulation treatment fails to meet a predetermined criteria; and
   after determining that the effect of the electrical stimulation treatment fails to meet the predetermined criteria, automatically performing the steps of:
   setting the second set of structural and functional information as the first set of structural and functional information;
   transdermally applying another electrical stimulation treatment to the portion of the patient's skin associated with the dysfunctional muscle tissue site;
   obtaining a new second set of structural and functional information for the dysfunctional muscle tissue site in a patient via the non-invasive ultrasound visualization process; and
   evaluating an effect of the another electrical stimulation treatment based on a comparison of the first set and the new second set of structural and functional information.

7. An apparatus for locating and diagnosing dysfunctional muscle tissues and for treating the dysfunctional muscle tissues, the apparatus comprising:
   a head unit; the head unit comprising:
   at least one electrode coupled to an electrical stimulation component; and a non-invasive imaging component for performing a non-invasive visualization process;
   wherein the head unit further comprises at least a first face, and the at least one electrode and the non-invasive imaging component are fixedly positioned on the same first face, such that the at least one electrode and the non-invasive imaging component can be simultaneously placed into contact with a patient's skin by positioning the first face adjacent to the patient's skin; and
   a controller coupled to the electrical stimulation component and the non-invasive imaging component, the controller comprising a processor configured for performing the following steps conducted without repositioning the first face with regard to the patient's skin, and therefore without moving the non-invasive imaging component and the electrode each fixedly positioned on the first face, the steps comprising:
obtaining, via the non-invasive imaging component, a first set of structural and functional information for a site of the dysfunctional muscle tissue in the patient; and,
without repositioning the first face, and therefore without moving the non-invasive imaging component and the electrode, transdermally applying, via the electrode and electrical stimulation component, a first electrical stimulation treatment to a portion of the patient's skin at the site of the dysfunctional muscle tissue;
thereafter obtaining, via the non-invasive imaging component, without repositioning the first face, and therefore without moving the non-invasive imaging component and the electrode, a second set of structural and functional information for the site of the dysfunctional muscle tissue in the patient; and
automatically evaluating an effect of the electrical stimulation treatment through the use of software to compare the first set of structural and functional information and the second set of structural and functional information; and
upon determining that the effect of the electrical stimulation treatment fails to meet a predetermined criteria, automatically performing the additional steps of:
setting the second set of structural and functional information as a new first set of structural and functional information;
transdermally applying another electrical stimulation treatment to the portion of the patient's skin associated with the site of dysfunctional muscle tissue;
obtaining a new second set of structural and functional information for the region of interest in a patient via the non-invasive visualization process; and
automatically evaluating an effect of the other electrical stimulation treatment based on a comparison of the new first set of structural and functional information and the new second set of structural and functional information;
wherein the processor is further configured for automatically repeating the electrical stimulation treatment based on the automatic evaluation of the new first set of structural and functional information and the new second set of structural and functional information until at least one result is achieved selected from the group consisting of reducing the dysfunctional muscle tissue, eradicating the dysfunctional muscle tissue, eliminating pain in the muscle tissue, healing injury in the muscle tissue, restoring normal function of the muscle tissue, and restoring range of motion of the muscle tissue.

8. The apparatus of claim 7, wherein the non-invasive visualization process comprises grayscale ultrasound imaging of the region of interest and at least one of Doppler imaging of the region of interest or sonoelastography of the site of the dysfunctional muscle tissue.

9. The apparatus of claim 7, wherein the functional information comprises at least one of stiffness information for the region of interest or blood flow information for the site of the dysfunctional muscle tissue.

10. The apparatus of claim 7, wherein the structural information comprises at least one of size, depth, location, and echogenicity of the region of interest, and location of anatomy adjacent to the site of the dysfunctional muscle tissue.

* * * * *